United States Patent [19]
Malkowska et al.

[11] Patent Number: 6,077,532
[45] Date of Patent: Jun. 20, 2000

[54] PHARMACEUTICAL ION EXCHANGE RESIN COMPOSITION

[75] Inventors: Sandra Therese Antoinette Malkowska, Ely; Derek Allan Prater, Milton; Stewart Thomas Leslie, Cambridge; Adrian Brown, Huntingdon; Trevor John Knott, Bishops Stortford, all of United Kingdom

[73] Assignee: Euro-Celtique, S.A., Luxembourg, Luxembourg

[21] Appl. No.: 09/029,151

[22] PCT Filed: Sep. 2, 1996

[86] PCT No.: PCT/GB96/02156

§ 371 Date: May 8, 1998

§ 102(e) Date: May 8, 1998

[87] PCT Pub. No.: WO97/09036

PCT Pub. Date: Mar. 13, 1997

[30] Foreign Application Priority Data

Sep. 1, 1995 [GB] United Kingdom ............... 9517883

[51] Int. Cl.⁷ .................. A61K 9/16; A61K 9/52; A61K 47/30
[52] U.S. Cl. ............ 424/457; 424/489; 424/501; 514/952
[58] Field of Search ................. 424/489, 501, 424/457, 470; 514/951–52, 962, 965

[56] References Cited

U.S. PATENT DOCUMENTS 3,627,583   12/1971   Troy et al. .

FOREIGN PATENT DOCUMENTS

| 0200252 | 12/1986 | European Pat. Off. ..... A61K 31/635 |
| 0328877 | 8/1989 | European Pat. Off. ........ A61K 47/00 |
| WO 9216209 | 10/1992 | WIPO .......................... A61K 31/435 |

OTHER PUBLICATIONS

P.H. List et al.: "Hagers Handbuch Der Pharmazeutischon Praxis; 4th edition, vol. 7, part A" 1971, Springer Gerlog, Berlin Haldelberg, New York XPQO–2026431; p. 712.

Primary Examiner—Edward J. Webman
Attorney, Agent, or Firm—Davidson, Davidson & Kappel, LLC

[57] ABSTRACT

A process is provided for preparing a granular pharmnaceutical ion exchange resin composition that is readily dispersible in water by granulating an ion exchange resin, having a pharmacologically active ingredient bound thereto, with a particulate sugar or sugar alcohol. The process is characterised by the use of an aqueous solution of a sugar or sugar alcohol as a granulating medium.

14 Claims, No Drawings

PHARMACEUTICAL ION EXCHANGE RESIN COMPOSITION

This application is a 371 of PCT/GB96/02156 filed Sep. 2, 1996.

The present invention relates to a process of preparing pharmaceutical ion exchange resin compositions.

European Patent Application Publication No. 368682 describes a process for the preparation of a pharmaceutical ion exchange resin composition that is readily dispersible in water comprising granulating an ion exchange resin having a pharmacologicaliy active ingredient bound thereto with a sugar or a sugar alcohol in the presence of sufficient water to facilitate granulation. Unit doses are prepared by filling e.g. capsules, sachets or other suitable containers with the granules. Although the product of EP 368682 is satisfactory when made at pilot scale of manufacture (ca. 10–12 kg), it has been found at production scale of manufacture (ca. 100 kg or more), that a variable level of pharmaceutically active ingredient is obtained in unit doses prepared from a single batch of granulate. For instance, in the case of an ion exchange resin composition containing morphine sulphate, unit doses prepared from one batch of granulate and with a desired morphine content of 20 mg may have morphine contents in the range of 18.5 to 23.5 mg and a mean content of 21 5 mg (coefficient of variations 8.3%).

One aim of the present invention is to provide a process for preparing a pharmaceutical ion exchange resin composition which can be used to prepare unit doses having a reduced inter-unit dose variability of the content of active ingredient This has, surprisingly, been achieved by using an aqueous solution of a sugar or sugar alcohol as a granulating medium instead of water.

According to the present invention there is provided a process for preparing a granular pharmaceutical ion exchange resin composition that is readily dispersible in water by granulating an ion exchange resin, having a pharmacologically active ingredient bound thereto, with a particulate sugar or sugar alcohol, characterised by the use of an aqueous solution of a sugar or sugar alcohol as a granulating medium.

The pharmaceutical ion exchange resin compositions prepared be the process of this invention disperse readily in water For example, dispersion readily occurs inside a minute upon stirring in sufficient water. Preferably a composition of this invention disperses with stirring with 60 seconds in at least 5, for instance 20 times its own weight in water.

The aqueous solution of sugar or sugar alcohol is conveniently added to a mixture of resin and particulate sugar or sugar alcohol during granulation.

Preferably the sugar or sugar alcohol in the granulating fluid is identical to the sugar or sugar alcohol with which the resin is granulated.

Preferably the sugar or the sugar alcohol present in the solution and present as solid has a molecular weight of from 90 to 550, especially from 150 to 370. The preferred sugars are mono- or di-saccharides and the preferred sugar alcohols are reduced mono- or di-saccharides. Suitable sugars/sugar alcohols are sucrose, dextrose, maltose, fructose, lactose, mannitol, sorbitol or, which is preferred, xylitol.

The particulate sugar/sugar alcohol granules is preferably finely divided, preferably having particle sizes of 600 microns or less. In a particularly preferred embodiment of the present process, at least 90% (by weight) of the particulate sugar/sugar alcohol granules will have particle sizes of 250 microns or less.

Preferably the sugar or sugar alcohol is present in the solution at a concentration of 40% w/w to 60% w/w, e.g. 45% w/w to 55% w/w most preferably about 50% w/w.

Preferably, the amount of granulating medium employed is from 1 to 20%, especially from 4 to 15%, by weight of the weight of the final dry weight of the complex/sugar, sugar alcohol mix. Once the drug-resin complex and the sugar/sugar alcohol have been granulated, the granules formed are then dried, preferably, until their water content is below 0.35% (by weight) (when measured by the Karl Fischer method of moisture analysis).

Any acidic or basic drug may be bound to the ion exchange resin. Preferably, however, active ingredients having a biological half life of 8 hours or less are used.

Suitable ingredients include i. Narcotic analgesics, such as codeine, dihydrocodeine, hydromorphone, morphine, pentazocine and propoxyphene, ii. Sympathomimetics, such as norephedrine and pseudoephedrine, iii. Antitussives, such as dextromethorphan, iv. Analgesics, such as aspirin and tramadol, v Antiemetics, such as metoclopramide, vi. Anticholinergics, such as atropine, ipratropium bromide and scopolamine, vii Muscle relaxants, such as cyclobenzaprine and papaverine, viii. Bronchodilators, such as salbutamol, terbutaline and theophylline, ix. Antibiotics, such as amoxycillin, ampicillin, azlocillin, bacampicillin, cefamandole, cefonicid, cefotaxime, cefotetan, cefoxitin, ceftriaxone, mezlocillin and piperacillin, x. Antidepressants, such as bupropion, nomifensine, and nortriptyline, xi. Antiasthmatics, such as cromolyn, xii. Antineoplastics, such as tamoxifen, xiii. Antiepileptics, such as valproic acid and phenvtoin, xiv Cardiovascular agents, such as propranolol.

Acid addition salts or if appropriate, alkali or alkaline earth metal salts of the above drugs would be particularly suitable for use in the present process.

Similarly, a wide range of cationic (for the basic drugs) or anionic (for the acidic drugs) exchange resins may be used to bind the active ingredient. Suitable ion exchange resins have acryiic, methacrylic, phenol-formaldehyde or dextran matrices. However, a preferred cationic ion exchange resin is a gel styrene-divinyl benzene sulphonic acid resin, such as Amberlite IR P69 (Trade Mark) and Dowex 50W-8 100–200 (Trade Mark).

The particle size and the degree of cross linking of the resin is determined by amongst other factors, the drug employed and the rate of drug release required. Preferably, however, the resin has a particle size of from 0.045 to 1 mm, especially from 0.045 to 0.5 mm. The preferred degree of cross-linking is from 2% to 16%, especially from 8% to 12%.

The amount of drug bound to the resin is also determined by the choice of drug, as well as by the resin employed. Preferable the weight ratio of bound drug to resin is from 1:3 to 2:1, especially from 2:3 to 3:2.

Adsorption of the drug onto the ion exchange resin particles is a well known technique as shown in GB 824337, GB 1218102 and U.S. Pat. No. 2,990,332 and demonstrated in the examples of EP-A 368682. In general, the drug is mixed with an aqueous suspension of the resin and the complex is then dried. Adsorption of the drug onto the resin is detected by an assay of the suspending fluid.

In a preferred form the process of the present invention provides drug resin complexes or granules which upon oral administration result in adsorption of the active ingredient from the gastro-intestinal tract enabling therapeutically effective blood levels of the active ingredient to be achieved, suitably the compositions are controlled release compositions and in their most preferred form enable therapeutically effective blood levels to be maintained upon dosing in at least 12 hourly intervals.

Optionally, the drug-resin complex or the granules may be film coated with a material that permits release of the drug from the composition at a controlled rate.

The film coat will generally include a water insoluble material such as (a) a wax, either alone or in admixture with a fatty alcohol, (b) shellac or zein, (c) a water insoluble cellulose derivative, especially ethyl cellulose, (d) a polymethacrylate, especially Eudragit (Trade Mark).

Preferably, the film coat comprises a mixture of the water insoluble material and a water soluble material. The ratio of water insoluble to water soluble material is determined by, amongst other factors, the release rate required and the solubility characteristics of the materials selected.

The water soluble material may be, for example, triacetin, propylene glycol, polyethylene glycol, polyvinylpyrrolidone or, which is preferred, a water soluble cellulose, such as hydroxypropyl cellulose, or especially, hydroxypropylmethyl cellulose.

Suitable combinations of water insoluble and water soluble materials for the film coat include shellac and polyvinylpyrrolidone or, which is preferred, ethyl cellulose and hydroxypropylmethyl cellulose.

Once the above processing is complete the composition may then be presented in a suitable dosage form, such as a capsule or a sachet. This is done simply by filling the capsule/sachet with the finished composition.

The present process and compositions prepared by the present process will now be described by way of example only,

COMPARATIVE EXAMPLE 1

A morphine sulphate controlled release resin was prepared as described in Example 1 of EP-A 368682.

56.98 kg milled xylitol having a particle size of 90% less than 200 μm and not more than 10% less than 51 μm, was blended with 4.62 kg of the morphine resin complex and 2.20 kg Xanthan gum in a high shear mixer/granulator for 12 minutes at impeller/chopper speeds of 1/1 with the gradual addition of 4.4 kg water over 19.5 minutes, The resulting granules were removed and partially dried in a fluid bed drier with inlet air at 60° C. The partially dried mass was passed through a 900 μm mesh screen and drying was continued in the fluid bed drier with an inlet air temperature of 60° C. until a moisture content of less than 0 35% w/w was achieved. The dried granules were then passed through a 630 μm screen after which they were blended with flavoring and coloring agents for 10 minutes in a Y-cone blender to provide Batch No. 1. The contents of this batch was used to fill 110,000 sachets such that each sachet represents a unit dose containing nominally 20 mg morphine sulphate The composition in each sachet was as follows:

| | mg |
|---|---|
| Morphine sulphate/Dowex W50 × 8 100–200 (Trade Mark) resin complex | 42.0 |
| Xylitol USNF milled | 518.0 |
| Xanthan gum USNF | 20.0 |
| Raspberry Flavour 52 354/TP 05.51 | 1.0 |
| Panceau 4R | 2.0 |

COMPARATIVE EXAMPLES 2 to 6

The process described in the Comparative Example 1 was repeated five times using the relative amounts of ingredients given below to provide Batches 2 to 6 respectively which were then used to prepare sachets having nominal strengths of morphine of 30 mg (Batches 2 and 3), 60 mg (Batch 4), 100 mg (Batch 5) and 200 mg (Batch 6).

| | mg |
|---|---|
| Morphine sulphate/Dowex W50 × 8 100–200 (Trade Mark) resin complex | 63.0 |
| Xylitol USNF milled | 497.0 |
| Xanthan gum USNF | 20.0 |
| Raspberry Flavour 52 354/TP 05.51 | 1.0 |
| Ponceau 4R | 2.0 |

EXAMPLES 1, 2 AND 3

The process of Comparative Example 1 was repeated three times except that the amount of milled xylitol added to the mixer granulator was 52.98 kg and 8 kg of a 50% w/w solution of xylitol was gradually added to the blend of morphine resin complex and milled xylitol over 18 minutes.

The resulting Batches 7, 8 and 9 respectively were used to prepare sachets containing nominally 20 mg morphine sulphate. The amount of material used per sachet was as follows:

| | mg |
|---|---|
| Morphine sulphate/Dowex W50 × 8 100–200 (Trade Mark) resin complex | 42.0 |
| Xylitol USNF milled | 482.0 |
| Xanthan gum | 20.0 |
| Xylitol USNF | 36.4 |
| Raspberry Flavour 52 354/TP 05.51 | 1.0 |
| Ponceau 4R | 2.0 |

EXAMPLES 4 to 7

The process of Example 1 was repeated four times using the relative amounts of ingredients given below to provide Batches 10 to 13 respectively which were then used to prepare sachets having nominal strengths of morphine in the range of 30 mg (Batch 10), 60 mg (Batch 11) 100 mg (Batch 12) and 200 mg (Batch 13).

| | mg |
|---|---|
| Morphine sulphate/Dowex W50 × 8 100–200 (Trade Mark) | 63.0 |
| Xylitol USNF milled | 458.0 |
| Xanthan gum USNF | 20.0 |
| Xylitol USNF | 38.6 |
| Raspberry Flavour 52 354/TP 05.51 | 1.0 |
| Ponceau 4R | 2.0 |

REFERENCE EXAMPLE 1 the various sachets obtained by the process described above were assayed for morphine content using an HPLC assay method (Spherisorb ODS-2 or equivalent column) with the following results:

| Batch | Mean Assay/Sachet (mg) | Range (mg) | Standard Deviation (mg) | Coefficient or Variation (%) |
|---|---|---|---|---|
| 1 | 21.53 | 18.42–23.48 | 1.782 | 8.28 |
| 2 | 32.12 | 30.02–33.47 | 1.170 | 3.64 |
| 3 | 31.70 | 29.94–33.00 | 1.126 | 3.55 |
| 4 | 66.55 | 62.73–69.69 | 2.650 | 3.98 |
| 5 | 102.0 | 90.15–121.2 | 9.928 | 9.73 |
| 6 | 205.5 | 194.7–211.2 | 4.959 | 2.24 |
| Granulation with xylitol solution | | | | |
| 7 | 20.25 | 19.60–20.86 | 0.346 | 1.71 |
| 8 | 20.62 | 19.86–21.15 | 0.392 | 1.90 |
| 9 | 20.91 | 20.65–21.49 | 0.270 | 1.29 |
| 10 | 32.48 | 31.87–33.43 | 0.425 | 1.31 |
| 11 | 65.61 | 63.97–66.76 | 0.881 | 1.34 |
| 12 | 110.2 | 104.6–112.5 | 2.125 | 1.93 |
| 13 | 204.7 | 197.0–212.9 | 4.301 | 2.10 |

We claim:

1. A process of preparing a granular pharmaceutical ion exchange resin composition that is readily dispersible in water comprising the step of granulating a mixture of an ion exchange resin, having a pharmaceutically active ingredient bound thereto, and a particulate sugar or sugar alcohol, with an aqueous solution of sugar or sugar alcohol as a granulating medium.

2. The process according to claim 1, wherein said aqueous solution of sugar or sugar alcohol is added to said mixture during said granulating step.

3. The process according to claim 1 wherein said sugar or sugar alcohol in the aqueous solution thereof is identical to the particulate sugar or sugar alcohol in said mixture.

4. The process according to claim 1 wherein said aqueous solution has a concentration of from 40% to 60% w/w of sugar alcohol.

5. The process according to claim 1 wherein said sugar or the sugar alcohol in said mixture and/or in said aqueous solution comprises sucrose, dextrose, maltose, fructose, lactose, mannitol, sorbitol or xylitol, preferably xylitol.

6. The process according to claim 1 wherein all of the sugar or the sugar alcohol particles have a particle size of 600 microns or less.

7. The process according to claim 6, wherein at least 90% (by wt) of the sugar or the sugar alcohol particles have a particle size of 200 microns or less.

8. The process according to claim 1 wherein said pharmaceutical composition contains from 25% to 99% (by weight) of the sugar or the sugar alcohol.

9. The process according to claim 1 wherein the amount of aqueous solution of sugar or sugar alcohol employed in the granulation is from 1% to 20% (by weight) of the final dry weight of the mixture.

10. The process according to claim 1 wherein after said granulating, said composition is dried until its water content is below 0.35% (by weight).

11. The process according to claim 1 further comprising the step of filling a capsule or a sachet with said composition.

12. The process according to claim 1 wherein said aqueous solution has a concentration of about 50% w/w, of sugar alcohol.

13. The process according to claim 1 wherein said composition contains from 70% to 95% (by weight) of the sugar or the sugar alcohol.

14. The process according to claim 1 wherein the amount of aqueous solution of sugar or sugar alcohol employed in the granulation is from 4% to 15%, (by weight) of the mixture.

* * * * *